United States Patent
Simonian et al.

(10) Patent No.: US 9,029,806 B2
(45) Date of Patent: May 12, 2015

(54) METHOD AND APPARATUS FOR TESTING LUMINESCENT FILMS

(75) Inventors: Dmitri Simonian, Sunnyvale, CA (US); Mikhail Fouksman, Emerald Hills, CA (US)

(73) Assignee: Koninklijke Philips N.V., Eindhoven (NL)

( * ) Notice: Subject to any disclaimer, the term of this patent is extended or adjusted under 35 U.S.C. 154(b) by 32 days.

(21) Appl. No.: 13/885,774

(22) PCT Filed: Dec. 19, 2011

(86) PCT No.: PCT/IB2011/055788
§ 371 (c)(1),
(2), (4) Date: May 16, 2013

(87) PCT Pub. No.: WO2012/085824
PCT Pub. Date: Jun. 28, 2012

(65) Prior Publication Data
US 2013/0313444 A1    Nov. 28, 2013

Related U.S. Application Data

(60) Provisional application No. 61/425,805, filed on Dec. 22, 2010.

(51) Int. Cl.
*G01N 21/25* (2006.01)
*G01N 21/64* (2006.01)
*G01N 21/27* (2006.01)
*G01N 21/59* (2006.01)
*G01N 21/47* (2006.01)

(52) U.S. Cl.
CPC .............. *G01N 21/64* (2013.01); *G01N 21/274* (2013.01); *G01N 21/59* (2013.01); *G01N 2021/4742* (2013.01); *G01N 2201/065* (2013.01)

(58) Field of Classification Search
CPC .................................................... G01N 21/6428
USPC ........................................................ 250/459.1
See application file for complete search history.

(56) References Cited

U.S. PATENT DOCUMENTS

| | | | |
|---|---|---|---|
| 5,044,754 A * | 9/1991 | Cicchiello et al. | 356/432 |
| 5,079,678 A | 1/1992 | Parker | |
| 5,406,070 A | 4/1995 | Edgar et al. | |
| 5,764,352 A | 6/1998 | Kappel et al. | |
| 5,929,994 A | 7/1999 | Lee et al. | |
| 5,963,335 A * | 10/1999 | Boutelle | 356/433 |
| 8,339,025 B2 * | 12/2012 | Nakamura et al. | 313/484 |
| 2004/0156981 A1 * | 8/2004 | Ohno et al. | 427/58 |

FOREIGN PATENT DOCUMENTS

| | | |
|---|---|---|
| DE | 2757196 A1 | 6/1979 |
| EP | 1688704 A1 | 8/2006 |
| GB | 2429865 A | 3/2007 |

* cited by examiner

*Primary Examiner* — David Porta
*Assistant Examiner* — Hugh H Maupin

(57) ABSTRACT

A structure for testing a luminescent film includes a Lambertian light source, an integrating sphere having an input port, and a measuring device. The Lambertian light source includes a mixing chamber having an input port and an output port, and a light emitter coupled to the input port. During testing the luminescent film is positioned between the output port of the mixing chamber and the input port of the integrating sphere. The measuring device is optically coupled to the integrating sphere.

19 Claims, 3 Drawing Sheets

METHOD AND APPARATUS FOR TESTING LUMINESCENT FILMS

BACKGROUND

1. Field of Invention

The present invention relates to a device and method for testing light emitted by and transmitted through a luminescent film.

2. Description of Related Art

Semiconductor light-emitting devices including light emitting diodes (LEDs), resonant cavity light emitting diodes (RCLEDs), vertical cavity laser diodes (VCSELs), and edge emitting lasers are among the most efficient light sources currently available. Materials systems currently of interest in the manufacture of high-brightness light emitting devices capable of operation across the visible spectrum include Group III-V semiconductors, particularly binary, ternary, and quaternary alloys of gallium, aluminum, indium, and nitrogen, also referred to as III-nitride materials. Typically, III-nitride light emitting devices are fabricated by epitaxially growing a stack of semiconductor layers of different compositions and dopant concentrations on a sapphire, silicon carbide, III-nitride, or other suitable substrate by metal-organic chemical vapor deposition (MOCVD), molecular beam epitaxy (MBE), or other epitaxial techniques. The stack often includes one or more n-type layers doped with, for example, Si, formed over the substrate, one or more light emitting layers in an active region formed over the n-type layer or layers, and one or more p-type layers doped with, for example, Mg, formed over the active region. Electrical contacts are formed on the n- and p-type regions.

A light emitting device is often combined with one or more wavelength converting materials such as phosphors to create white light. All or only a portion of the light emitted by the LED may be converted by the wavelength converting materials. Unconverted light emitted by the LED may be part of the final spectrum of light, though it need not be. Examples of common combinations include a blue-emitting LED combined with a yellow-emitting phosphor, a blue-emitting LED combined with green- and red-emitting phosphors, a UV-emitting LED combined with blue- and yellow-emitting phosphors, and a UV-emitting LED combined with blue-, green-, and red-emitting phosphors. Other wavelength converting materials may be added to tailor the spectrum.

SUMMARY

It is an object of the invention to provide a device and method for testing a luminescent film.

In embodiments of the invention, a structure for testing a luminescent film includes a Lambertian light source, an integrating sphere having an input port, and a measuring device. The Lambertian light source includes a mixing chamber having an input port and an output port, and a light emitter coupled to the input port. During testing the luminescent film is positioned between the output port of the mixing chamber and the input port of the integrating sphere. The measuring device is optically coupled to the integrating sphere.

A method according to embodiments of the invention includes positioning a Lambertian light source proximate a first surface of a luminescent film, positioning an opening in an integrating sphere proximate a second surface of the luminescent film, illuminating a portion of the film with the Lambertian light source, and measuring a property of light from the luminescent film collected by the integrating sphere. In some embodiments, after measuring a property of light from the luminescent film, a property of a portion of the luminescent film is altered in response.

In embodiments of the invention, a structure for testing a luminescent film includes a light source, a light collection device, and a measuring device. During testing the luminescent film is positioned between the light source and the light collection device. The measuring device is optically coupled to the light collection device.

DETAILED DESCRIPTION

In accordance with embodiments of the invention, devices and method for testing the properties of light from luminescent films are provided. One example of a luminescent film is formed as follows: one or more conventional powder phosphors are mixed with a binder such as acrylic or silicone to achieve a target phosphor density. The phosphor/binder sheet is formed to have a target thickness, for example by spinning the mixture on a flat surface or molding the phosphor sheet. Phosphor may be mixed with a binder in liquid form which is then cured or dried to form a flexible luminescent film. Another example of a luminescent film is a powder phosphor or other wavelength converting material that is sintered into a ceramic. Such a film may be sintered with the desired thickness or may be sawn from a thicker ceramic phosphor. The luminescent film may be flexible, as in the case of a phosphor/binder film, stretchable, or rigid, as in the case of a ceramic phosphor. Other wavelength converting materials besides phosphors may be used, such as for example dyes, quantum dots, or optically-pumped semiconductor materials such as III-V or II-VI materials.

After testing, the luminescent film may be attached or laminated directly to a suitable light source, or it may be spaced apart from the light source, for example as part of a display. Examples of suitable light sources include but are not limited to blue- or UV-emitting III-nitride LEDs and laser diodes. Any other suitable light source may be used with the luminescent films tested by the devices and methods described herein.

Figure 1:
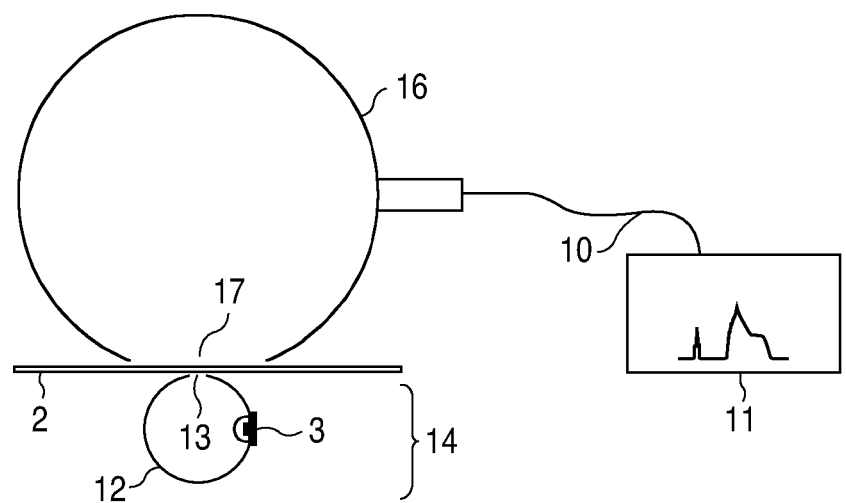
FIG. 1 illustrates one example of a device for testing the properties of a luminescent film.

FIG. 1 illustrates a first device for testing the properties of light from a luminescent film. In the device illustrated in FIG. 1, a small area of luminescent film 2 is illuminated by a Lambertian light source 14 placed in close proximity to film 2 on one side of film 2. For example, the distance between port 13 of light source 14 and luminescent film 2 is less than 500 µam in some embodiments and less than 100 µm in some embodiments. Lambertian light source 14 includes a light emitter 3 positioned in an opening in a mixing chamber 12. Light exiting the mixing chamber at port 13 illuminates luminescent film 2. Light emitter 3 may be, for example, a blue LED similar to an LED with which luminescent film 2 is to be paired after testing, or any other suitable light source. The peak wavelength of light emitter 3 may be matched to that of a light source with which luminescent film 2 is to be paired after testing, in some embodiments. In any of the devices described herein, the light emitter 3 or the entire light source 14 may be temperature controlled. Mixing chamber 12 may be, for example, a hollow sphere, the inside of which is coated with a highly reflective scattering material. Port 13 may optionally be covered with a transparent window such as glass, sapphire, quartz, or plastic.

A device for measuring the light is positioned on the other side of luminescent film 2. The measured light includes light emitted by the light source 14 and scattered by luminescent film 2 at the same wavelength, and light absorbed by luminescent film 2 and reemitted over a different wavelength range.

Luminescent film 2 is positioned between a port 13 of mixing chamber 12 and a port 17 of an integrating sphere 16. An integrating sphere is a hollow cavity with the interior coated with a highly diffuse reflecting material to cause uniform scattering. Integrating spheres are known in the art. One or both of port 13 and 17 may be knife-edge ports in some embodiments. In some embodiments, port 17 is larger than port 13, though they may be the same size or port 17 may be smaller than port 13. In some embodiments, the separation between ports 17 and 13 is no more than 1 mm. In some embodiments, the separation between portions 17 and 13 is such that luminescent film 2 is in sliding engagement with one or both ports. The surfaces of ports 17 and/or 13 in sliding engagement with luminescent film 2 may be electrically conductive.

Light captured by integrating sphere 16 may be coupled to a suitable measuring device 11 by, for example, a suitable light transmitting structure 10 such as a fiber bundle. Alternatively, measuring device 11 may be directly coupled to integrating sphere 16. Measuring device 11 may be, for example, a spectrometer or a photo colorimeter. Measuring device 11 may measure properties of the captured light such as, for example, the color, peak wavelength, full width at half maximum of the spectrum, total radiant flux, and/or luminous flux. Measuring device 11 may also measure the ratio of scattered, unconverted photons to converted photons. In some embodiments, the light source or a reference source may emit long-wavelength light that is not wavelength-converted by luminescent film 2 (for example, light at a peak wavelength greater than 650 nm in some embodiments) and measuring device 11 measures light through luminescent film 2, in order to characterize scattering by luminescent film 2.

Figure 2:
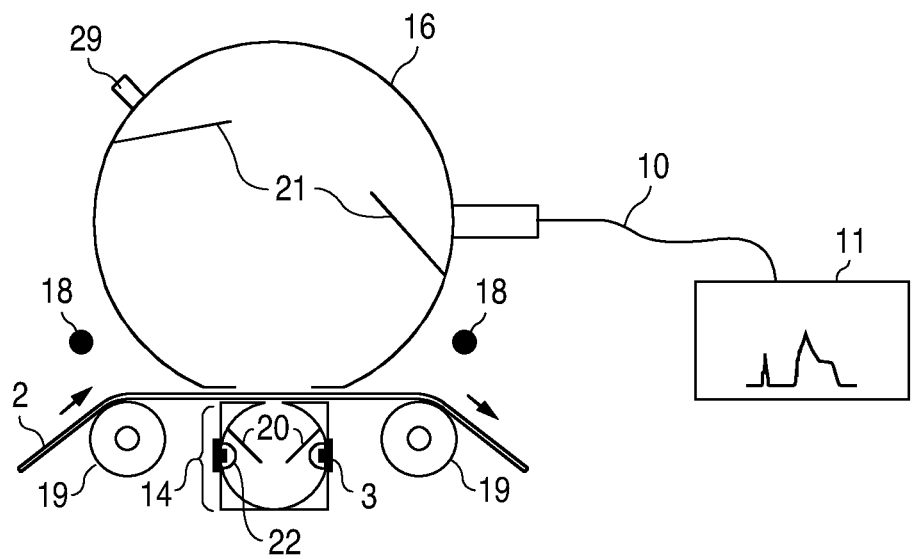
FIG. 2 illustrates the device of FIG. 1 including guiding rollers and ionizing bars.

The device illustrated in FIG. 2 includes a Lambertian light source 14, integrating sphere 16, light transmitting structure 10, and measuring device 11 as in the device illustrated in FIG. 1. Light source 14 may include a reference white light 22 which is used to monitor the stability of the instrument. Before testing a luminescent film 2, the spectra of one or both of source 3 and reference light 22 are measured and compared to known values. In the device illustrated in FIG. 2, one or more guiding rollers 19 are used to move and position luminescent film 2 between ports 13 and 17. Anti-static ionizing bars 18 may be positioned proximate the measuring device 11 and/or integrating sphere 16 to reduce tribocharging and to reduce the amount of dust in the ambient. Integrating sphere 16 and/or mixing chamber 12 may include optional baffles 21 and 20, respectively, to improve light mixing in each chamber. The device of FIG. 2 may include an optional calibrated source 29 optically coupled to integrating sphere 16. Calibrated source 29 is used to calibrate measuring device 11.

In some embodiments, integrating sphere 16 is positioned on a mechanism that allows for removal and replacement without affecting alignment. For example, integrating sphere 16 may be mounted on a hinge which allows integrating sphere 16 to be lifted at the beginning of a production run. One end of a roll of a luminescent film 2 is placed over port 13, then integrating sphere 16 is brought back into its original position with luminescent film 2 disposed between port 17 and port 13. In some embodiments, integrating sphere 16 is positioned on kinematic or magnetic mounts for ease of removal and reproducible replacement. In some embodiments, one or both of integrating sphere 16 and mixing chamber 12 are mounted on springs which push ports 13 and 17 together in order to maintain sliding contact of both ports with luminescent film 2. An advantage to the use of springs is that ports 13 and 17 can be disposed in sliding contact with luminescent film 2 regardless of the thickness of luminescent film 2.

Figure 3:
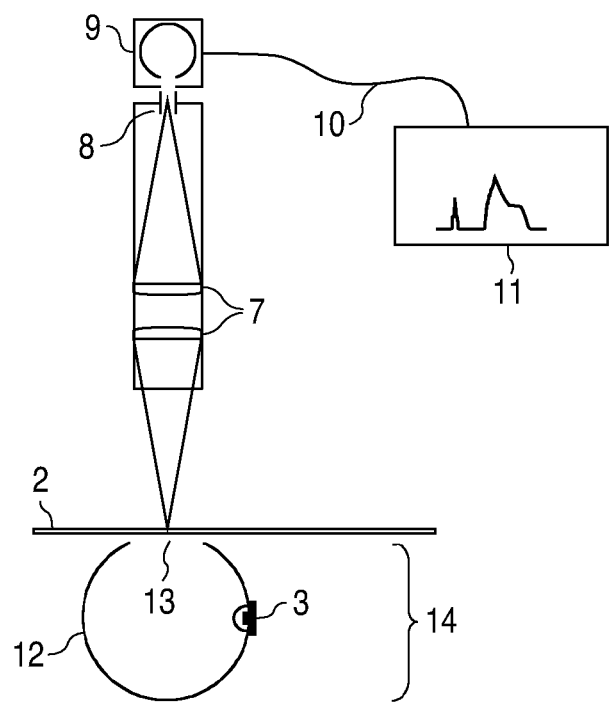
FIG. 3 illustrates an example of a device for testing the properties of a luminescent film including a mixing chamber and collection optics.
Figure 4:
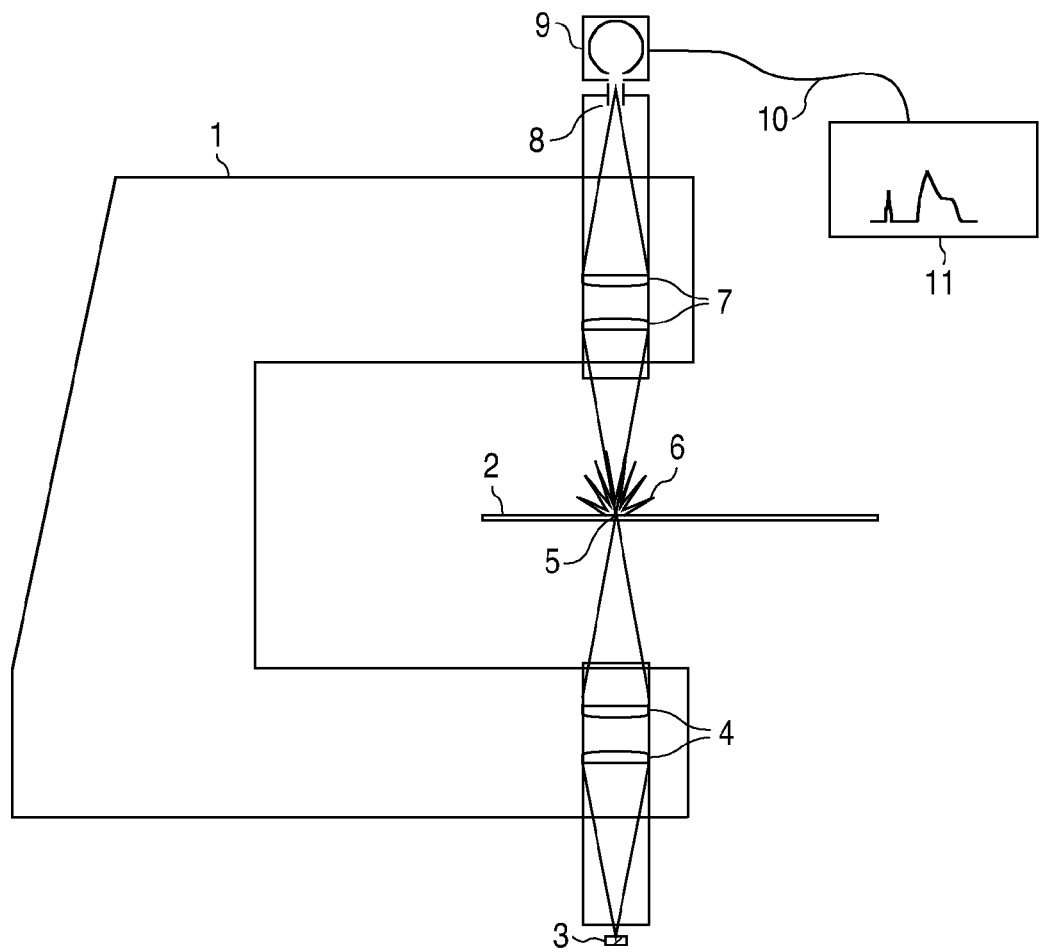
FIG. 4 illustrates an example of a device for testing the properties of a luminescent film including imaging optics and collection optics.

The devices illustrated in FIGS. 1 and 2 may have advantages over the devices illustrated in FIGS. 3 and 4. In the devices of FIGS. 1 and 2, the luminescent film 2 is illuminated by a Lambertian source, as it would be if combined after testing with a conventional LED as a light source. Substantially all the light emitted from the tested region of luminescent film 2 is collected by integrating sphere 16, which may improve the accuracy of the measurement. In addition, vertical and torsional displacements of luminescent film 2 may be minimized by mechanical constraints provided by ports 13 and 17, and by optional guiding rollers 19. For example, in some embodiments, one or both of ports 13 and 17 are large-area flanges, wider than 25 mm in diameter in some embodiments. The flanges flatten luminescent film 2, thereby removing any artifacts in light measurement having to do with unwanted changes in illumination geometry. Further, the devices of FIGS. 1 and 2 may be less sensitive to ambient light than the devices illustrated in FIGS. 3 and 4.

In the device illustrated in FIG. 3, luminescent film 2 is illuminated as in the devices of FIGS. 1 and 2, by a Lambertian light source 14 including a light emitter 3 coupled to a light mixing chamber 12 having a port 13, which may be covered by a transparent window. All or a portion of the light from the portion of luminescent film 2 illuminated by light from port 13 is collected by collection optics 7 in field aperture 8. The size of the sampled spot is determined by the size of field aperture 8. Light passes through field aperture 8 into a measurement head 9, where it is then directed by a light transmitting structure 10 to a measuring device 11, as described above in reference to FIGS. 1 and 2.

In the device illustrated in FIG. 4, light from light emitter 3 is reimaged by imaging optics 4 such as for example a doublet pair, onto a spot 5 on luminescent film 2. Spot 5 is between 1 and 3 $mm^2$ in some embodiments. Wavelength-converted and unconverted scattered light emitted from spot 5 is collected by collection optics 7 and directed to field aperture 8. Each of imaging optics 4 and collection optics 7 may be, for example, singlets made of fused silica or another UV-transparent material. The size of field aperture 8 is selected such that only light emitted by illuminated spot 5 is collected in field aperture 8, an opening in a measurement head 9. Light collected by measurement head 9 is directed by a light transmitting structure 10 to a measuring device 11, as described above in reference to FIGS. 1 and 2.

The axis of illumination of luminescent film 2 by light emitter 3 is normal or substantially normal to the plane of luminescent film 2 in some embodiments. The illuminated beam is nearly collimated with a numerical aperture (N.A.) below 0.2 in some embodiments. Similarly, the axis of collection optics 7 is normal or substantially normal to the plane of luminescent film 2 in some embodiments. In some embodiments, the acceptance cone created by collection optics 7 is narrow such that the collection N.A. is less than 0.2 in some embodiments and between 0.05 and 0.15 in some embodiments.

In some embodiments, imaging optics 4 and light emitter 3, and collection optics 7, aperture 8, and measurement head 9 are attached to a frame 1. Frame 1 is attached to a translation stage so frame 1 can be moved to sample different parts of a stationary luminescent film 2. In some embodiments, frame 1 is stationary and luminescent film 2 is moved, for example by rollers as illustrated in FIG. 2. In some embodiments, a testing device such as one of the structures illustrated in FIGS. 1-4 is a part of a luminescent film production line. The device may move in widthwise direction with respect to the luminescent film, while the luminescent film moves through the production line.

The device illustrated in FIG. 4 can be modified for use with a larger illuminated spot 5. In such a device, collection optics 7 include a pair of lenses in a telecentric configuration. The pair of lenses are separated by a distance such that their back focal planes coincide, and an angular aperture positioned in the back focal plane defines the acceptance cone.

In embodiments where the luminescent film 2 is stationary during measurement, the probed area of luminescent film 2 is equal to the spot size. In the devices of FIGS. 1, 2, and 3, the spot size is the size of port 13; in the device of FIG. 4, the spot size 5 is determined by imaging optics 4. In some embodiments, the probed area is increased by measuring when the measurement apparatus (integrating sphere 16 or collection optics 7) is moving relative to luminescent film 2, for example as described above in reference to FIG. 4. The effective probed area is approximately $A=sv\tau$, where s is the spot diameter, v is the velocity of the relative motion of the luminescent film 2, and $\tau$ is the measurement or integration time. The effective probed area can be varied by selecting the velocity and integration time.

Figure 5:
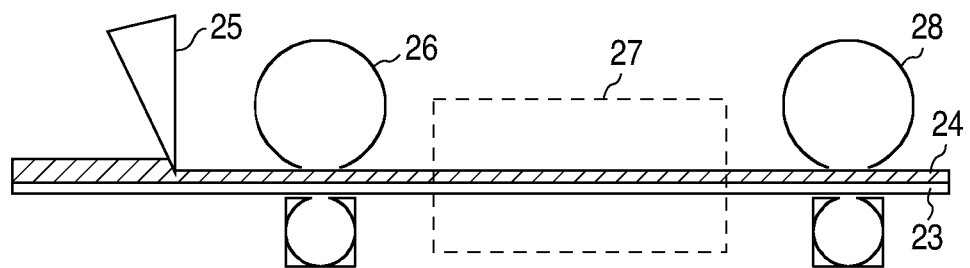
FIG. 5 illustrates a production line for making a luminescent film.

FIG. 5 illustrates a device for producing a luminescent film targeted to specific values of light conversion properties such as, for example, color point. In the production line illustrated in FIG. 5, the luminescent film includes a substrate film 23 that is coated with a luminescent layer 24 by any of a variety of methods known in the art such as, for example, application by a blade coater 25 as illustrated in FIG. 5, or by a spray process. The coated film may pass through one or more optional post-coating steps 27, which may include, for example, drying, partial curing, application of a protective film, and/or bar-code marking. A tester 28 according to embodiments of the invention, which may be one of the devices illustrated in FIGS. 1-4, is placed at the end of a luminescent film production line illustrated in FIG. 5. Tester 28 measures one or more properties of light from the finished luminescent film, such as the color point. The properties of the luminescent film may be monitored only, to ensure adequate process control, or the properties of the already-tested luminescent film and/or the luminescent film remaining in the production run may be adjusted based on measurements from tester 28 (and/or optional tester 26 described below), in order to achieve desired properties in the luminescent film. For example, the thickness of the luminescent material, the amount of luminescent material in the luminescent film, or the coating parameters may be adjusted based on measurements from tester 28 and/or tester 26.

In some embodiments, an additional optional tester 26 according to embodiments of the invention, which may be one of the devices illustrated in FIGS. 1-4, is placed downstream from coater 25. An experimentally pre-determined relationship between measurements of testers 26 and 28 is used to convert a color target for the final film as measured by tester 28 into the corresponding color target for tester 26. The reading by tester 26 is brought to a target value by adjusting suitable parameters of the coating process, at the beginning of or during a luminescent film production run. Tester 26 may be a tester according to an embodiment of the present invention, or may be a different type of tester whose target reading will be calculated from its pre-determined relationship to the spectral measurement of the finished luminescent film by tester 28. Examples of properties measured by tester 26 include but are not limited to absorbance at a particular wavelength in a transmission or reflection mode, light scattering signature, film thickness, light interferometric profile, and/or electrical impedance.

Having described the invention in detail, those skilled in the art will appreciate that, given the present disclosure, modifications may be made to the invention without departing from the spirit of the inventive concept described herein. Therefore, it is not intended that the scope of the invention be limited to the specific embodiments illustrated and described.

What is being claimed is:

1. A structure for testing a luminescent film, the structure comprising:
   a first tester, the first tester comprising:
      a Lambertian light source the Lambertian light source comprising a mixing chamber having an input port and an output port;
      a light emitter coupled to the input port;
      an integrating sphere having an input port;
      at least one baffle disposed in one of the mixing chamber and the integrating sphere; and
      a measuring device; and
   a second tester disposed downstream relative to the luminescent film of the first tester,
   wherein during testing the luminescent film is positioned between the output port of the mixing chamber and the input port of the integrating sphere;
   wherein the measuring device is optically coupled to the integrating sphere
   wherein the second tester measures a property of the luminescent film.

2. The structure of claim 1 wherein during testing, the output port of the mixing chamber is spaced less than 500 μm from the luminescent film.

3. The structure of claim 1 wherein during testing, the output port of the mixing chamber is spaced less than 1 mm from the input port of the integrating sphere.

4. The structure of claim 1 wherein the light emitter is an LED configured to emit blue light.

5. The structure of claim 1 wherein during testing the luminescent film is in sliding engagement with at least one of the input port of the integrating sphere and the output port of the mixing chamber.

6. The structure of claim 1 wherein at least one of the input port of the integrating sphere and the output port of the mixing chamber is a knife-edge port.

7. The structure of claim 1 further comprising rollers positioned to guide the luminescent film.

8. The structure of claim 1 wherein the luminescent film comprises phosphor disposed in a flexible material.

9. The structure of claim 1 wherein the measuring device is one of a spectrometer and a photo colorimeter.

10. A method comprising:
   positioning a Lambertian light source proximate a first surface of a luminescent film;
   positioning an opening in an integrating sphere proximate a second surface of the luminescent film;

illuminating a portion of the film with the Lambertian light source;

measuring a property of light from the luminescent film collected by the integrating sphere; and after measuring a property of light from the luminescent film, altering a property of a portion of the luminescent film in response to the measurement.

11. The method of claim 10 wherein the light from the luminescent film comprises light from the Lambertian light source transmitted through the luminescent film at the same wavelength and light from the Lambertian light source absorbed by the luminescent film and emitted by the luminescent film at a different wavelength.

12. The method of claim 10 wherein altering a property of a portion of the luminescent film comprises changing an amount of luminescent material in the luminescent film.

13. The method of claim 10 wherein the Lambertian light source comprises a mixing chamber having an input port and an output port.

14. The method of claim 13 wherein during testing, the output port of the mixing chamber is spaced less than 500 µm from the luminescent film.

15. The method of claim 13 wherein during testing, the output port of the mixing chamber is spaced less than 1 mm from the input port of the integrating sphere.

16. The method of claim 13 wherein the light emitter is an LED configured to emit blue light.

17. The method of claim 13 wherein during testing the luminescent film is in sliding engagement with at least one of the input port of the integrating sphere and the output port of the mixing chamber.

18. The method of claim 13 wherein at least one of the input port of the integrating sphere and the output port of the mixing chamber is a knife-edge port.

19. The method of claim 10 wherein the luminescent film comprises phosphor disposed in a flexible material.

* * * * *